(12) United States Patent
Tohma et al.

(10) Patent No.: US 7,936,912 B2
(45) Date of Patent: May 3, 2011

(54) SAMPLE IMAGING APPARATUS, SAMPLE ANALYZING APPARATUS, AND SAMPLE IMAGING METHOD

(75) Inventors: Ryuichi Tohma, Akashi (JP); Hideyuki Higuchi, Kobe (JP); Masanori Nakaya, Kobe (JP)

(73) Assignee: Sysmex Corporation, Kobe (JP)

( * ) Notice: Subject to any disclaimer, the term of this patent is extended or adjusted under 35 U.S.C. 154(b) by 1163 days.

(21) Appl. No.: 11/540,156

(22) Filed: Sep. 29, 2006

(65) Prior Publication Data

US 2007/0077550 A1  Apr. 5, 2007

(30) Foreign Application Priority Data

Sep. 30, 2005 (JP) ................................. 2005-287463

(51) Int. Cl.
*G06K 9/00* (2006.01)
(52) U.S. Cl. ....................................................... 382/133
(58) Field of Classification Search .................. 382/133
See application file for complete search history.

(56) References Cited

U.S. PATENT DOCUMENTS 7,068,832 B1 * 6/2006 Price et al. ..................... 382/137
2003/0027342 A1 * 2/2003 Sheridan et al. ................ 436/43

FOREIGN PATENT DOCUMENTS

JP  60-162955  8/1985
JP  07-020124  1/1995

* cited by examiner

*Primary Examiner* — John B Strege
(74) *Attorney, Agent, or Firm* — Brinks Hofer Gilson & Lione (57) ABSTRACT

A sample imaging apparatus comprising: a sample image obtainer for obtaining an image of a sample smeared on a sample holder, the sample holder comprising an identification part which comprises identification information of the sample; an identification detector for detecting the identification information; an identification part image obtainer for obtaining an identification part image comprising an image of at least a portion of the identification part; an output device; and a controller for controlling the output device, such that the image of the sample and the identification part image are output when the identification detector can not detect the identification information is disclosed. A sample analyzing system, a sample analyzing apparatus, and a sample imaging method are also disclosed.

20 Claims, 8 Drawing Sheets

Automatic imaging device controller processing flow

SAMPLE IMAGING APPARATUS, SAMPLE ANALYZING APPARATUS, AND SAMPLE IMAGING METHOD

This application claims priority under 35 U.S.C. §119 to Japanese Patent Application No. JP2005-287463 filed Sep. 30, 2005, the entire content of which is hereby incorporated by reference.

FIELD OF THE INVENTION

The present invention relates a sample imaging apparatus, a sample analyzing apparatus, and a sample imaging method for obtaining an image of a sample smeared on a sample holder.

BACKGROUND

Automatic analyzers of blood cells are known that are capable of automatically and simultaneously making blood cells counts and examining morphological blood cell types (for example, refer to Japanese Laid-Open Patent Publication No. 60-162955). This automatic analyzer is configured by an automatic blood cell classifying system that prepares a blood sample by smearing part of a blood sample on a slide glass and staining the smear, then identifies and classifies a blood cell image of the blood sample, and an automatic blood cell calculating system that counts the number of blood cells in a constant volume taken from the blood sample, and the analyzer simultaneously reports the results of the blood cell calculation and blood cell classification.

More specifically, in this automatic analyzer, the automatic blood cell classifying system uses an ID reader to read the ID of the blood sample to which an ID has been appended beforehand by an ID maker, and thereafter uses a camera to make an image of the blood cell that has been enlarged by an optical microscope, calculates the characteristics of the blood cells in a characteristics extraction circuit, and classifies each type of blood cell. Also in this automatic analyzer, the automatic blood cell calculating system counts the blood cell based on detection signals of hemoglobin concentration, white blood cells, red blood cells, and platelets. Then, predetermined signals are sent from a microcomputer to an I/O controller regarding abnormal samples that exceed a normal range for the number of cells that has been previously set.

The I/O controller confirms the ID of the abnormal sample, and issues instruction to double or triple the number of blood cells used for blood cell classification of the blood sample matching the ID, or change the method of examining the cells of the blood sample. Specifically, since there is a high ratio of abnormal cells at the ends of the smear surface, heightened detection of abnormal cells can be accomplished using a method that examines this specific range in detail.

In this automatic blood cell analyzer, it is difficult to specify the ID of a blood specimen when the ID of a blood sample can not be read by the ID reader due to the faintness of the ID printing or the like.

SUMMARY OF THE INVENTION

The scope of the present invention is defined solely by the appended claims, and is not affected to any degree by the statements within this summary.

A first aspect of the present invention is a sample imaging apparatus comprising: a sample image obtainer for obtaining an image of a sample smeared on a sample holder, the sample holder comprising an identification part which comprises identification information of the sample; an identification detector for detecting the identification information; an identification part image obtainer for obtaining an identification part image comprising an image of at least a portion of the identification part; an output device; and a controller for controlling the output device, such that the image of the sample and the identification part image are output when the identification detector can not detect the identification information.

A second aspect of the present invention is a sample analyzing apparatus comprising: a sample image obtainer for obtaining an image of a sample smeared on a sample holder, the sample holder comprising an identification part which comprises identification information of the sample; a sample analyzing section for analyzing the sample based on the image of the sample obtained by the sample image obtainer; an identification detector for detecting the identification information from the identification part; an identification part image obtainer for obtaining an identification part image comprising an image of at least a portion of the identification part; an output device; and a controller for controlling the output device, such that an analysis result obtained by the sample analyzing section and the identification part image obtained by the identification part image obtainer are output when the identification detector can not detect the identification information.

A third aspect of the present invention is a sample imaging method for obtaining an image of a sample smeared on a sample holder, comprising: attempting detection of identification information of the sample from an identification part of the sample holder; obtaining an identification part image comprising an image of at least a portion of the identification part at least when the identification information can not be detected; obtaining an image of the sample; and outputting the image of the sample and the identification part image when the identification information can not be detected.

BRIEF DESCRIPTION OF THE DRAWINGS

FIG. 8 shows an example of a display screen shown on a display, such as blood cell image data and blood identification and classification results and the like.

DETAILED DESCRIPTION OF THE PREFERRED EMBODIMENTS

The preferred embodiments of the present invention are described hereinafter with reference to the drawings.

<Structure of a Blood Image Analyzing System>

Figure 1:
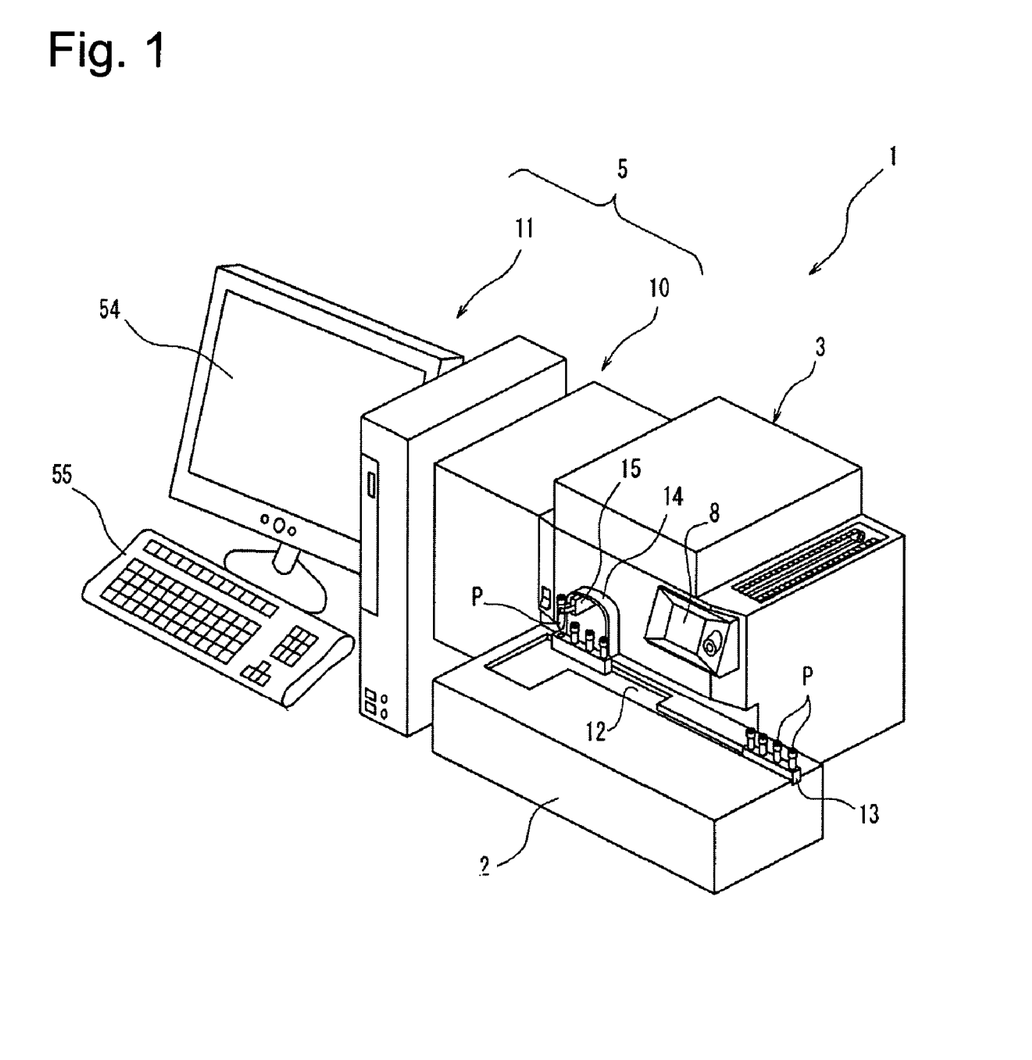
FIG. 1 is a perspective view showing the exterior structure of a blood image analyzing system.
Figure 2:
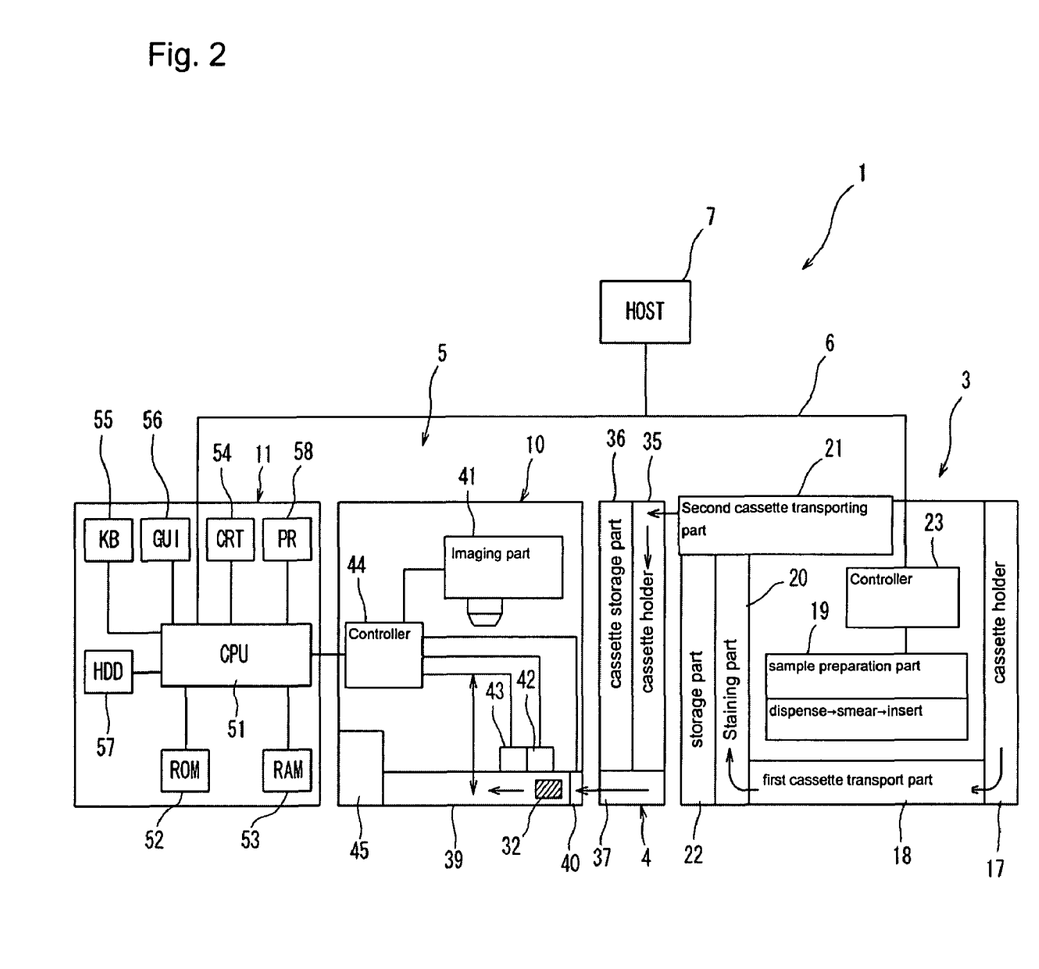
FIG. 2 is a block diagram showing the system structure of the blood image analyzing system.

FIG. 1 shows the exterior structure of a blood image analyzing system 1 as an embodiment of the present invention, and FIG. 2 shows the structure of that system.

The blood image analyzing system 1 of the present embodiment is installed in a facility that performs blood examinations such as a hospital or the like, and is configured by a transporting device 2 for transporting test tubes P, a sample preparing device 3 for automatically preparing blood samples, a cassette supplying unit 4 (refer to FIG. 2), and an automatic analyzer 5 for imaging the components of the blood samples and classifying blood cells and the like. Each of these devices 1 through 5 are connected to a host computer 7 (refer to FIG. 2) via a network (LAN) 6.

<Exterior Structure of Each Device>

Among the devices 1 through 5, the automatic analyzer 5 processes digital images of a blood sample prepared by the sample preparing device 3 and automatically classifies the blood cells. The sample preparing device 3 prepares samples to be automatically analyzed in the analyses performed by the automatic analyzer 5, and prepares two types of samples as visual inspection samples to be analyzed by human inspection.

As shown in FIG. 1, the sample preparing device 3 is provided with case that has a touch panel 8 disposed on right end of the front surface as an operation part, and the transporting device 2 is arranged in front of this case. The automatic analyzer 5 is disposed on the left side of the sample preparing device 3. The automatic analyzer 5 is configured by an automatic imaging device 10 which is described later, and a blood image analyzer 11 that is a personal computer.

As shown in FIG. 2, the controllers of the sample preparing device 3 and the blood image analyzer 11 are connected to the host computer 7 via the previously mentioned network.

As shown in FIG. 1, the transporting device 2 is configured by a flat, oblong case that has a long transporting channel 12 formed in a lateral direction on the top surface, and a sample rack 13 for holding blood-filled test tubes P is accommodated in the transporting channel 12. The sample rack 13 is automatically transported along the transporting channel 12. A hand member 15 is retractably used to receive the test tube P from the transporting device 2 is provided at the receiving inlet 14 provided at the front left side of the sample preparing device 3.

Thus, when a sample rack 13 holding the test tubes P is placed at the right end of the transporting channel 12 of the transporting device 2, the sample rack 13 is automatically transported to the left side and arrives at the receiving inlet 14, and one test tube P is extracted by the hand member 15 and introduced onto the interior of the sample preparing device 3.

<Sample Preparing Device>

As shown in FIGS. 1 and 2, the sample preparing device 3 is configured by a cassette holder 17 that holds a sample cassette 32 (refer to FIG. 5), a first cassette transporting part 18 for moving a cassette within the holder 17 into the sample preparing device 3, and sample preparing part 19 for performing a sample preparing process on a sample plate 25 (refer to FIGS. 4 and 5) and inserting the plate 25 in the cassette 32 that passes through the transporting part 18.

The sample preparing device 3 is further provided with a staining section 20 that performs a staining process on the sample plate 25 held in the sample cassette 32, a second cassette transporting part 21 that moves the sample cassette 32 outside the device after the staining process, storing section 22 for holding the cassette 32 that accommodates the samples for visual inspection and analysis by human inspection, and a controller 23 for controlling the operation of each section. The cassette 32 that accommodates the sample to be used for automatic analysis by the automatic analyzer 5 is transported to a cassette receiving area of the cassette supply unit 4 by the second cassette transporting section 21.

Figure 4:
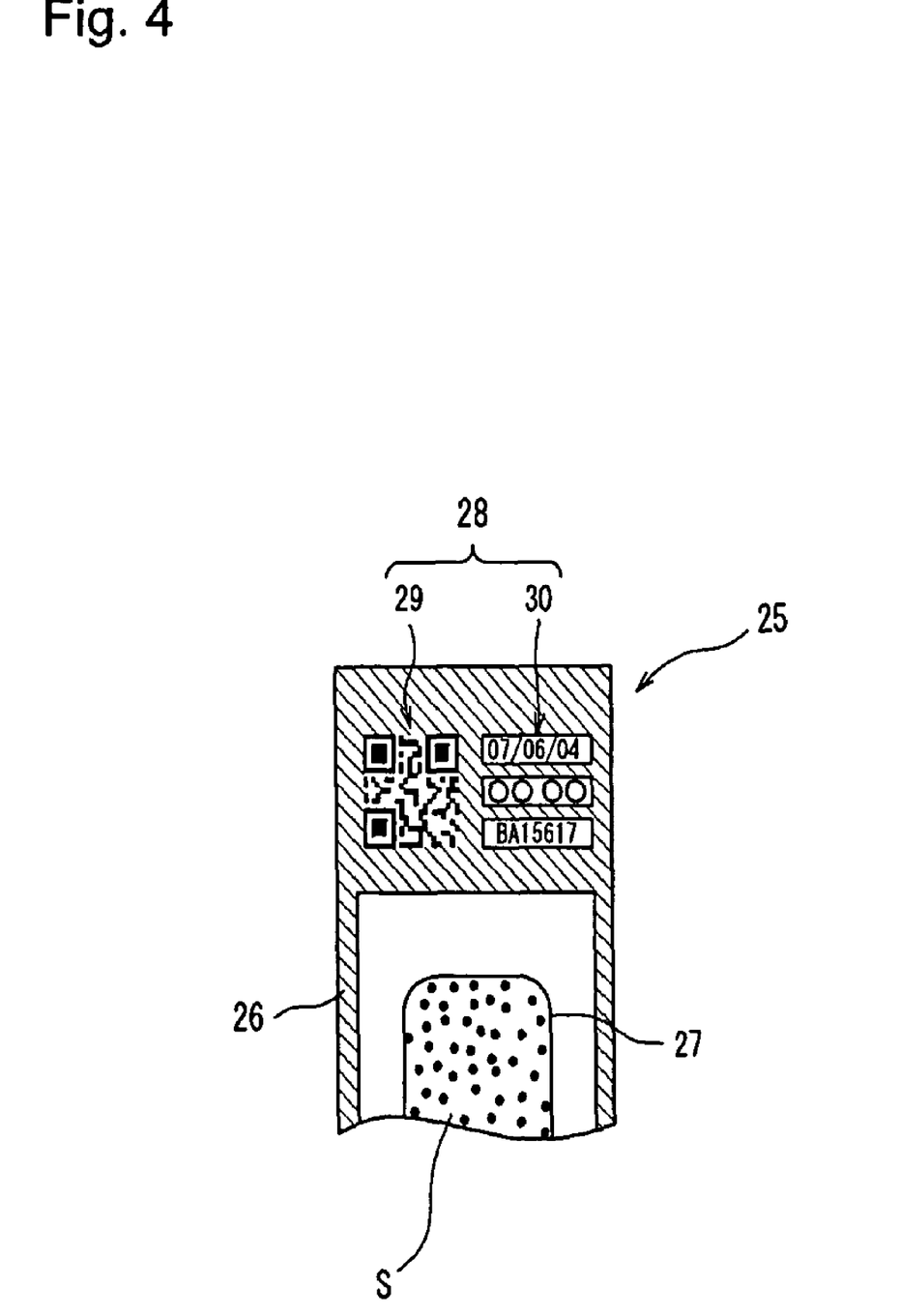
FIG. 4 is a frontal view of the top half of a sample plate.
Figure 5:
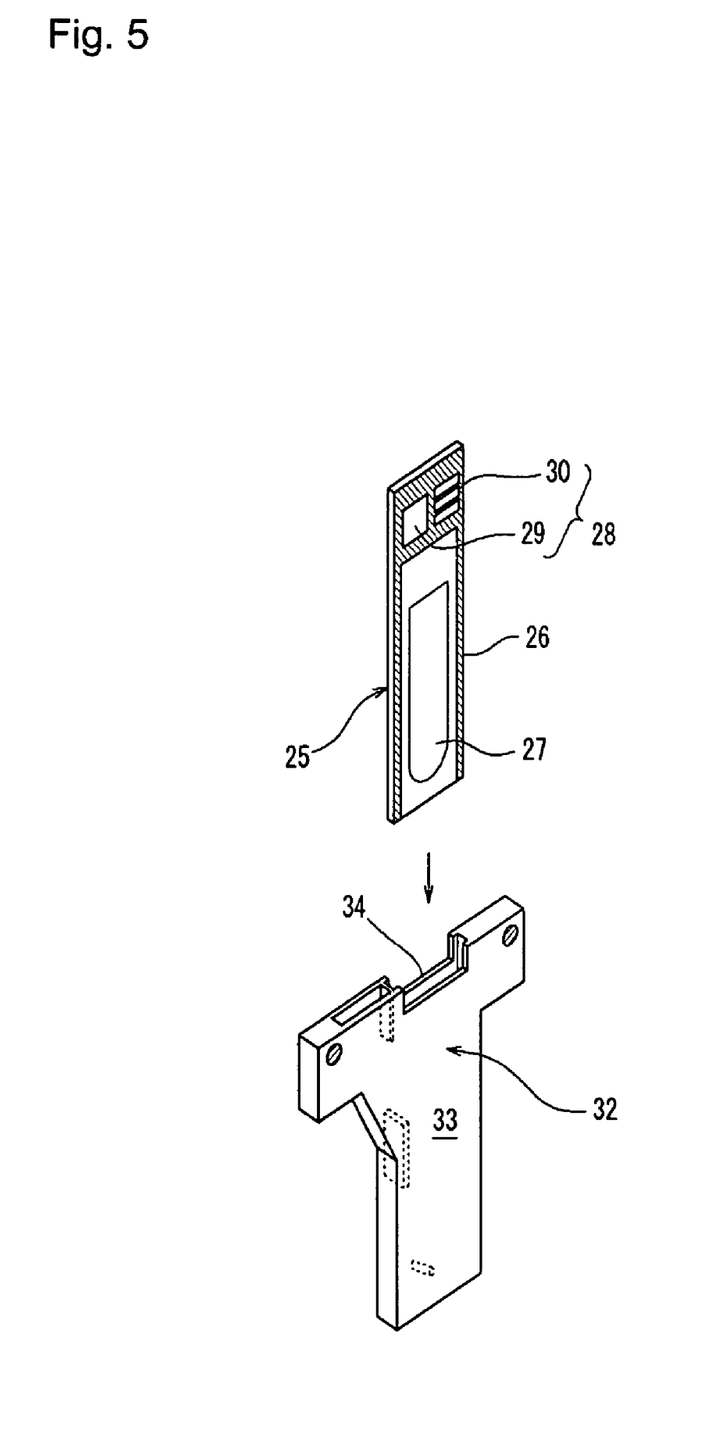
FIG. 5 is a perspective vie-v of the sample plate and sample cassette.

As shown in FIGS. 4 and 5, the sample plate 25 is provided with a plate body 26 formed in a rectangular frame-like shape, and a sample smearing section 27 as a sample holding body within the frame of the plate body 26. At the top end of the plate body 26 is provided an identification part 28 for recording identification information such as date, sample provider, ID number and other information (sample related information) regarding the sample. A blood sample S of the sample is smeared in the sample smearing section 27.

The identification part 28 includes two types of display parts 29 and 30 displayed on the left and right at the top end of the plate body 26. One of these (Left side in FIG. 4) is the code display area 29 in which a two-dimensional barcode that includes identification information is displayed, and the other (right side in FIG. 4) is the text information area 30 in which is displayed text information that includes identification information.

In the example in the drawing, the date on which the sample was prepared, the name of the sample provider and ID number are entered sequentially from the top in the text information area 30. Furthermore, a one-dimensional barcode may also be used in the code display area 29.

As shown in FIG. 5, the sample cassette 32 has a flat case body 33 formed in a T-shape. An insertion slot 34 is formed in the center part at the top end of the case body 33 for the insertion of the sample plate 25, and the insertion slot 34 is formed by notching downward as viewed from the top. Therefore, the sample plate 25 can be accommodated in the sample cassette 32 in a condition in which only the identification part 28 is exposed to the outside by inserting the sample slid 25 facing the insertion slot 34. Although not shown in the drawing, a barcode that includes an ID number that matches the sample plate 25 may be adhered to the test tube P.

As shown in FIG. 2, a sample preparing part 19 has a blood suctioning and dispensing, blood smearing function, and sample plate 25 inserting function. That is, the sample preparing part 19 has the function of suctioning blood from a test tube P brought to it by the hand member 15, and dripping the blood onto the sample smearing section 27 of the sample plate 25, and smearing the dripped blood on the sample smearing section 27. After smearing, the sample plate 25 is inserted in the sample cassette 32 passing through the first cassette transporting part 18, so as to be integrated with the sample cassette 32.

Although not shown in the drawing, the sample preparing part 19 also has the function of reading at least the ID number among the identification information of the test tube P and sample plate 25, and the controller 23 of the sample preparing device 3 instructs the sample preparing part 19 to perform the sample preparing operation on the sample plate 25 that has the same ID number as the test tube P.

<Cassette Supply Unit>

As shown in FIG. 2, the cassette supply unit 4 is provided with a cassette holding part 35 that holds a sample cassette 32 that has a stained sample plate 25 and has been transported from the sample preparing device 3, a cassette storing part 36 disposed downstream from the holding part 35, and a cassette supplying part 37. The sample cassette 32 that contains a sample plate 25 accommodated in the sample cassette holding part is moved from the cassette supplying part 37 to the sample plate removal part 40 of the automatic imaging device 10. The sample cassette 32 from which the sample plate 25 has been removed in the sample plate removing part 40 is stored in the cassette storing part 36 by the cassette supplying part 37.

<Automatic Imaging Device>

As shown in FIG. 2, the automatic analyzer 5 of the present embodiment is provided with an automatic imaging device 10 that has the function of enlarging and imaging a blood sample S of a specimen, and a blood image analyzer 11 that performs image processing necessary for identification and counting of cells, and both the devices 10 and 11 are connected so as to be capable of mutually communicating.

The automatic imaging device 10 is provided with a sample plate removing part 40 for removing the sample plate 25 from the sample cassette 32 that has been supplied from the cassette supplying unit 4, a sample plate transporting part 39 for transporting the sample plate 25 that has been removed from the sample plate removing part 40 into the device, an imaging part 41 for enlarging and imaging a blood image smeared on the sample smearing section 27 of the sample plate 25 that has been transported by the sample plat transporting part 39, and a sample plate holding part 45 for holding the imaged sample plate 25. The cassette accommodating the sample plate 25 is held in the sample plate holding part 45.

The automatic imaging device 10 is further provided with a first reading means 42, which is a barcode reader for acquiring identification information such as the sample ID number and the like by reading a two-dimensional barcode recorded on the barcode display part 29 of the sample plate 25 passing through the sample plate transporting part 39, and a second reading means 43, which is a CCD camera or the like for imaging the text information area 30 of the sample plate 25 that is passing through the same transporting part 39.

The imaging part 41 has built in a microscope capable of enlarging and observing a blood sample S smeared on the sample smearing section 27, a CCD camera for imaging an image (blood component image or cell image) of white blood cells and other blood cells contained in the sample, and an image memory for storing the RGB color images output from the camera after having been subjected to analog-to-digital conversion.

The control of the imaging part 41 and other types of controls in the automatic imaging device 10, and communication controls for data transfer to the network side over the network are controlled by the controller 44 provided in the automatic imaging device 5.

Figure 3:
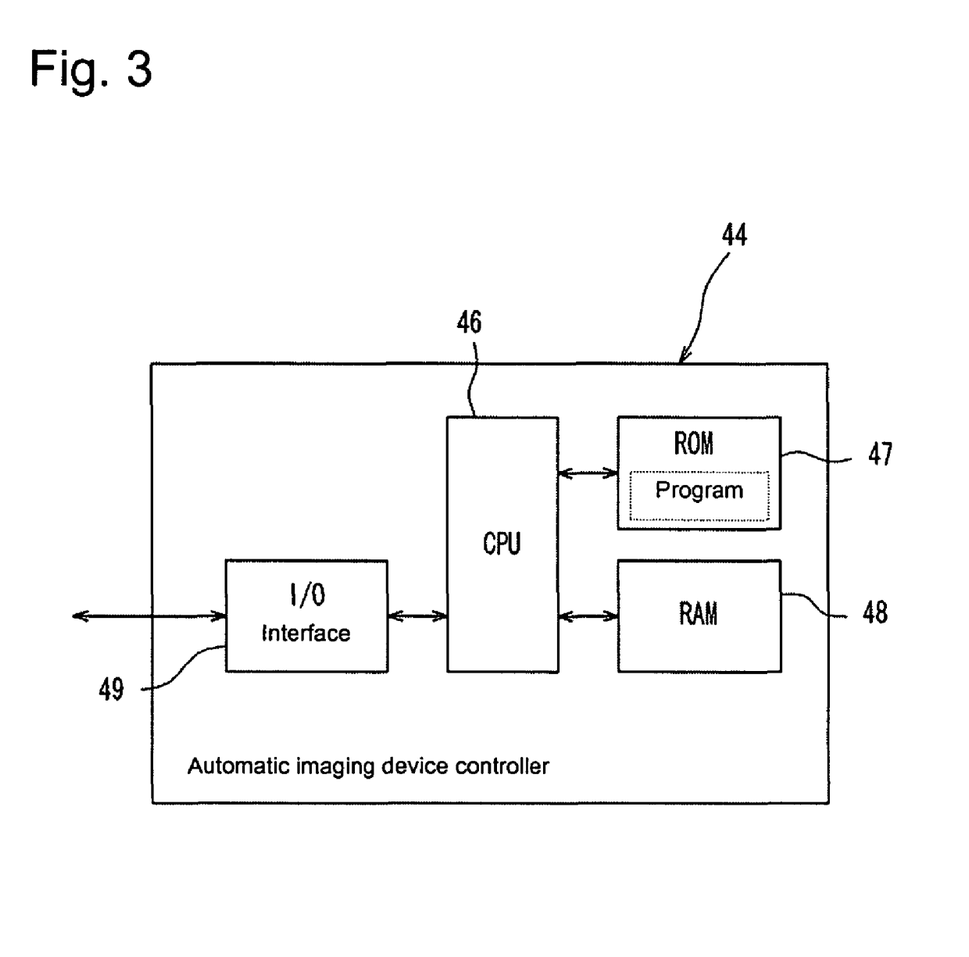
FIG. 3 is a block diagram of the controller of an automatic imaging device.

The controller 44 of the automatic imaging device 10 is configured by a CPU 46, ROM 47, RAM 48, and I/O interface 49 as shown in FIG. 3. An operating system and control program for controlling the operation of the imaging part 41, and data required to execute the control program are stored in the ROM 47.

The CPU 46 may load the control program in the RAM 48, or execute the control program directly from the ROM 47. Thus, the result data processed by the CPU 46 are sent to the various parts of the automatic imaging device 10 or an external device (blood image analyzer 11 or the like) outside the device 10 via the I/O interface 49, and the data required for the processing by the CPU 46 are received from the various parts of the automatic imaging device 10 or from an external device to the device 10 through the I/O interface 49. The CPU 46 is capable of performing the control operation of the flow chart in FIG. 6, which is described later, by executing the control program.

<Blood Image Analyzer>

As shown in FIG. 2, the blood image analyzer 11 is provided with a CPU 51, ROM 52, RAM 53, display device 54 such as a CRT or liquid crystal display or the like, input devices such as a keyboard (including specialized keyboard) 55 and mouse 56, and hard disk 57 as a large capacity storage device. Although not shown in FIG. 1, a printer 58 is connected to the blood image analyzer 11.

The ROM 52 stores an operating system and a control program for executing the imaging process and cell identification and classification processes performed by the analyzer 11, and data needed to execute these programs.

The CPU 51 may load the control program in the RAM 53, or execute the control program directly from the ROM 52. Thus, the result data processed by the CPU 51 are sent to an external device (automatic imaging device 10 or the like) outside the blood image analyzer 11 over a network that is not shown in the drawing, and the data required for the processing by the CPU 51 are received from the external device of the blood image analyzer 11 over the network that is not shown in the drawing.

The CPU 51 of the blood image analyzer 11 executes the control program to perform data processing of the blood cell images, calculate the characteristics needed recognize and classify of the blood cells, and identify and classify the blood cells based on these characteristics. The characteristics extraction process is performed by dividing the pixels of the sample image of the white blood cells into pixels related to the nucleus, pixels related to the cytoplasm, and other pixels.

The classification process uses parameters of characteristics of the cytoplasm to identify the type of object blood cell, and performs a blood cell count and classifies the blood cells.

For example, the classification process of the white blood cells (nucleated blood cells) classifies the object blood cells as six types of mature white blood cells (rod-like nucleus neutrophils, segmented nucleus neutrophils, eosinophils, basophils, lymphocytes, monocytes) and erythroblasts. The six types of mature white blood cells are normal nucleated blood cells, and three types of immature white blood cells and erythroblasts are abnormal nucleated cells.

Furthermore, the CPU 51 of the blood image analyzer 11 is capable of outputting, by various methods, blood images (blood cell images), cell identification and classification results (analysis results), and the image data of the text information area 30 imaged by the second reading means 43. These data are displayed on the display 54 by a display screen, an example of which is shown in FIG. 8, or the data may be stored on the hard disk 57 for review, or may be transmitted to the host computer 7 over the network.

Figure 8:
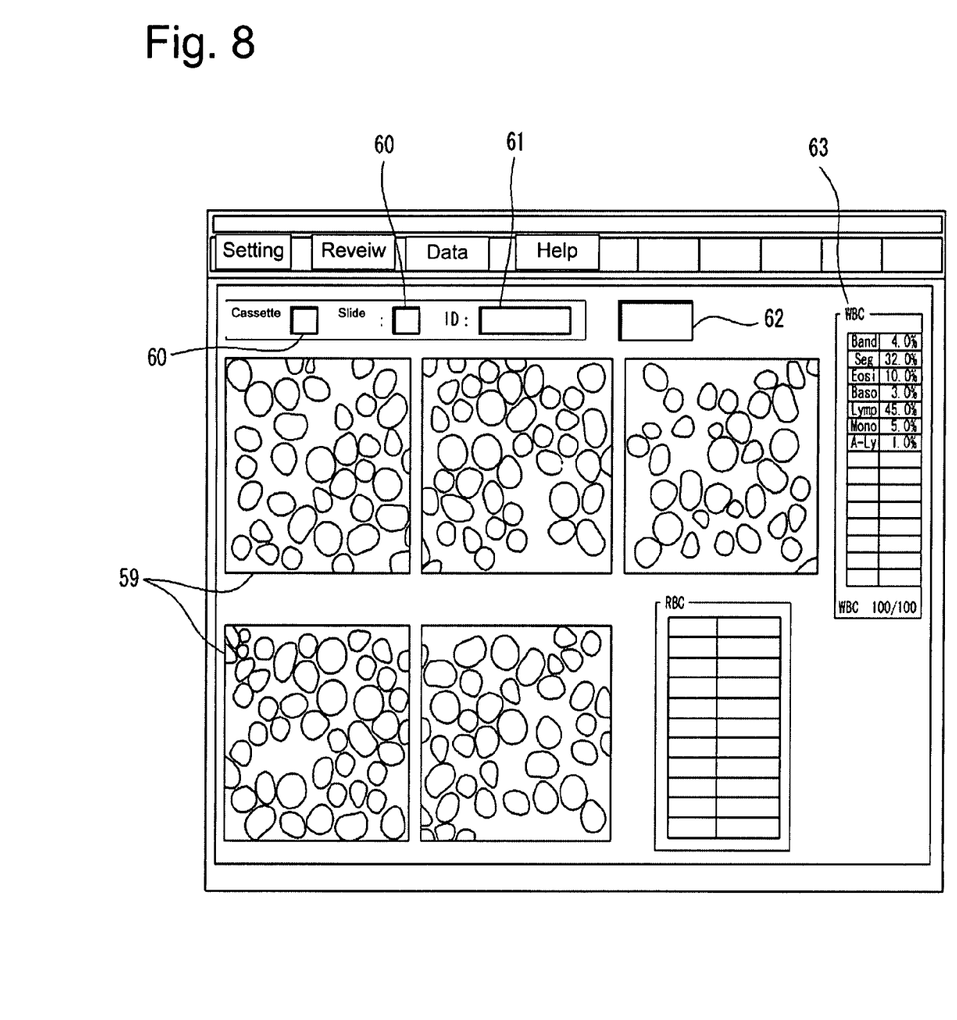

FIG. 8 shows an example of a display screen that shows the blood cell image data, the blood identification number and blood classification result. In this display screen, there are five display windows 59 for showing blood cell images. A display box 60 is provided at the top left of the display screen and is used for displaying the cassette number and slide (sample) number, and on the adjacent right side is a display box 61 for displaying the ID number. Furthermore, at the adjacent right side of the display box 61 used for the ID number is a display box 62 for displaying image data (image) of the text information area 30. On the far right side of the display screen is provided a display box 63 for displaying the WBC (white blood cell) classification result. Blood images of blood smeared on the sample smearing section 27 of the sample plate 25 imaged by the automatic imaging device 10 are displayed in the display windows 59. The slide (sample) number and cassette number of the cassette accommodating the sample plate 25 are displayed in the display box 60. The ID number of the sample plate 25 or a provisional ID number described later is displayed in the display box 61. An image of the text information area 30 of the sample plate 25 imaged by the second reading means 43 is displayed in the display window 62. The classification result of the WBC (white blood cell) classified by the blood image analyzer 11 is displayed in the display box 63.

<Automatic Imaging Device Processing Flow>

The processing flow of the automatic imaging device 10 is described below with reference to FIG. 6.

Figure 6:
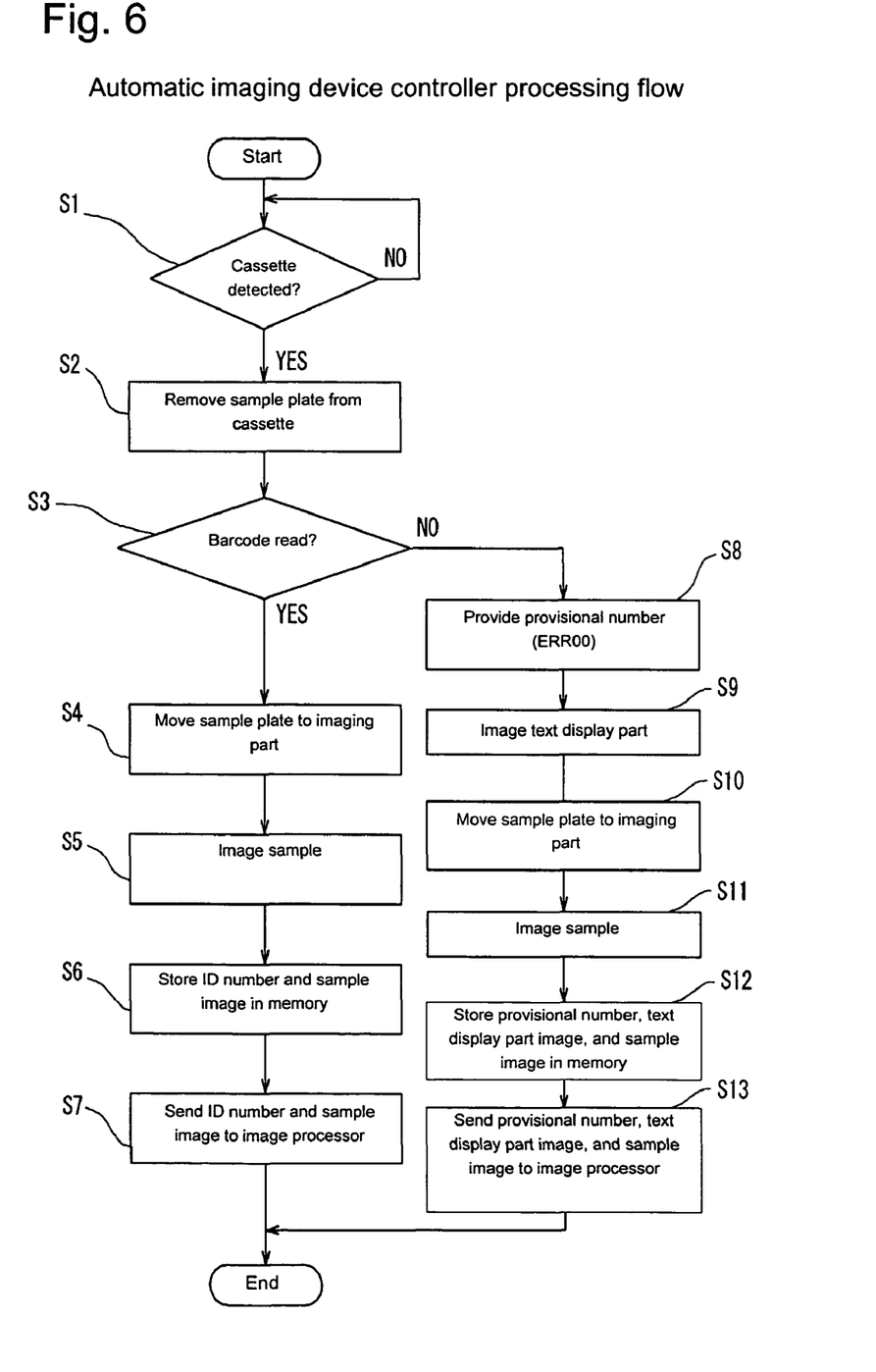
FIG. 6 is a flow chart showing the processing sequence of the automatic imaging device.

As shown in FIG. 6, when a sample cassette 32 is detected by a sensor (not shown in the drawing) provided in the sample plate removing part 40 of the automatic imaging device 10 (step S1), the sample plate 25 is removed from the sample cassette 32 (step S2). Thereafter, the barcode affixed to the barcode part 29 of the sample plate 25 is read by the first reading means 42, which is a barcode reader, and a determination is made as to whether or not the reading was properly accomplished (step S3).

When the barcode reading has been properly accomplished, the sample plate 25 is moved to the imaging part 41 (step S4), then the blood sample S smeared in the sample smearing section 27 is imaged in the imaging part 41 (step S5). Thereafter, the ID information that includes the ID number acquired by the first reading means 42 and the image data of the sample image obtained by the imaging part 41 are stored in the memory (step S6), and all the data are transmitted to the blood image analyzer 11 (step S7).

When the barcode reading can not be performed for any reason such as unclear printing or the like, a provisional ID number (for example, the code ERR indicating and error and a twelve digit number) are provided for the sample plate 25 (step S8). Thereafter, the text information area 30 of the sample plate 25 is imaged by the second reading means 43, which is a CCD camera or the like (step S9), then the sample plate 25 is sent to the imaging part 41 by the sample plate transporting part 39 (step S10), and the blood sample S is imaged in the imaging part 41 (step S11).

Subsequently, the provisional ID number, image data of the text information area 30, and blood image data of the sample image obtained by the imaging part 41 are stored in memory (step S12), and all the data is sent to the blood image analyzer 11 (step S13).

Although the second reading means 43 images the entirety of the text information area 30 in the present embodiment, only imaging the area of the ID number of the text information area 30 is also possible, as is imaging the entirety of the identification part 28. Although the date, name, and ID number are recorded in the text information area 30 in the present embodiment, the name alone may also be recorded, or only the name of the hospital and date of hospitalization of the sample provider may be recorded insofar as such information identifies the blood sample used by the automatic analyzer 5.

<Blood Image analyzer Processing Flow>

The processing flow of the blood image analyzer 11 is described below with reference to FIG. 7.

Figure 7:
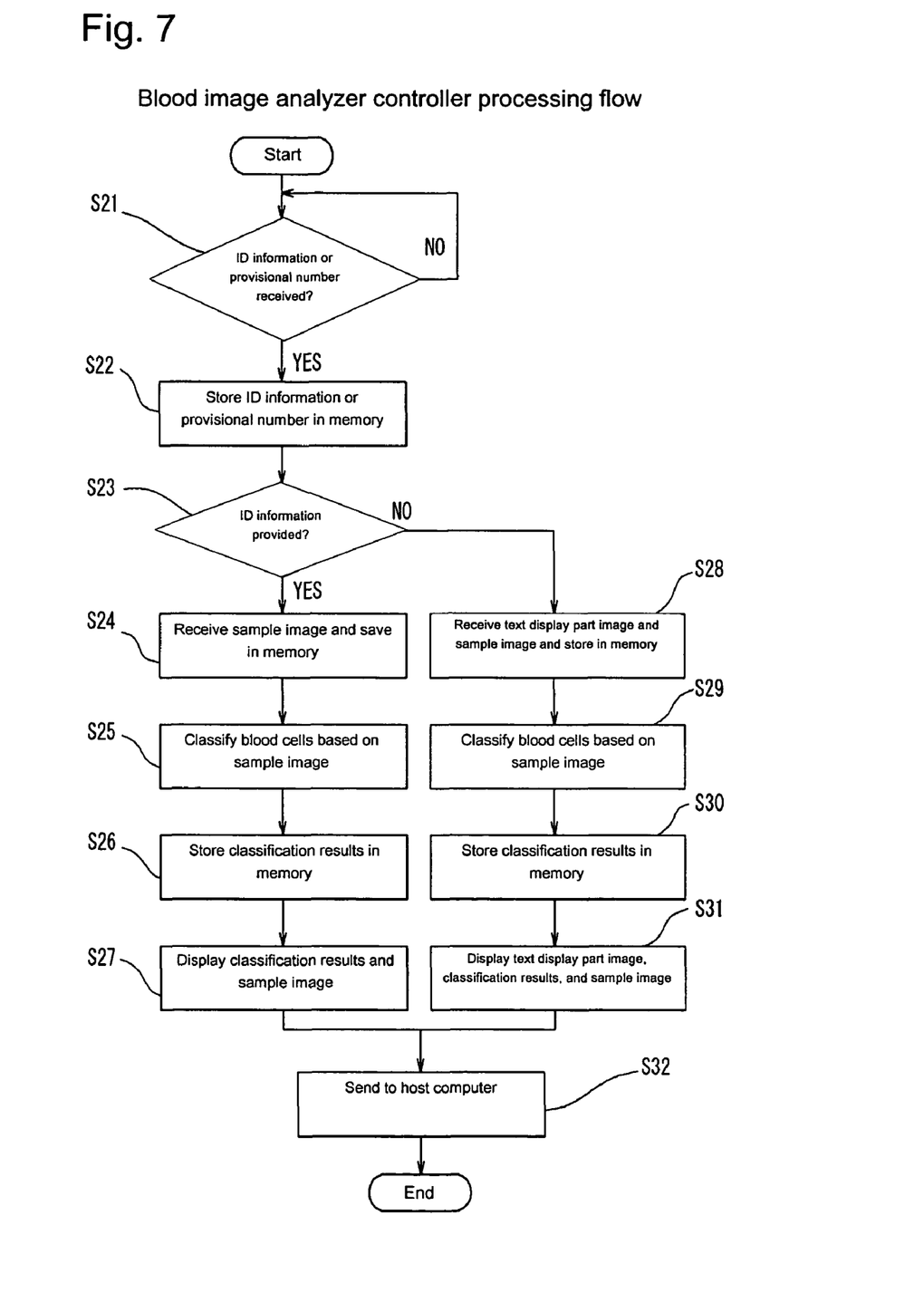
FIG. 7 is a flow chart showing the processing sequence of the blood image analyzer.

As shown in FIG. 7, when the primary identification information or ID number is first received in the blood image analyzer 11 from the automatic imaging device 10 (step S21), the received information is stored in memory (step S22) and a determination is made as to whether the ID number in the received information is a normal ID number read by the first reading means 42 or a provisional ID number (ERR00) that is provided when there is an error in the reading by the first reading means 42 (step S23).

When a proper ID number has been detected, the image data of the blood sample S are received and stored in memory (step S24), the blood cells are classified based on the image data of the blood sample S (step S25), and the classification results are stored in memory (step S26). Thereafter, the image data of the blood sample S and the classification results are displayed on the display 54 with the screen shown in FIG. 8 (step S27), and the data are sent to the host computer 7 (step S32).

In this case, the proper ID number is shown in the display box 61 used for the ID number and nothing is displayed in the display box 62 used for the text information area 30 in the display screen shown in FIG. 8.

When, however, a provisional ID number (ERR00) has been detected, the image data of the blood sample S and the image data of the text information area 30 are received and stored in memory (step S28), the blood cells are classified based on the image data of the blood sample S (step S29), and the classification results are stored in memory (step S30). Thereafter, the image data of the blood sample S, the image data of the text information area 30, and the classification results are displayed on the display 54 with the screen shown in FIG. 8 (step S31), and the data are sent to the host computer 7 (step S32).

In this case, the provisional ID number (ERR00) is shown in the display box 61 used for the ID number and the image data of the text information area 30 are displayed in the display box 62 used for the text information area 30 in the display screen shown in FIG. 8. The blood image analyzer 11 is constructed such that a user of the blood image analyzer 11 looking at the display screen shown in FIG. 8 can confirm a proper ID number from the image data of the text information area 30 displayed in the display box 62, and using the keyboard 55 and mouse 56 the user can input a proper ID number in the display box 61 that displays the provisional ID number.

Thus, according to the automatic analyzer 5 of the present embodiment, since the image data of the text information area 30 imaged by the second reading means 43 are output together with the image data of the blood sample S and the blood cell classification results to the host computer 7 and the display device 54 even when the first reading means 42 can not read the barcode, it is possible to match the provider (patient) and the sample plate 25 that was used for the blood cell classification and the image data of the blood sample S. Therefore, the image data of the examined sample plate 25 need not be wastefully re-examined, and mistakes regarding the provider of the sample plate 25 can be prevented before they occur.

Since a provisional ID number (ERR00) that can be discriminated from a normal ID number is provided in the automatic analyzer 5 of the present embodiment, misreading by the first reading means 42 can be understood by the presence of the provisional ID number. Then, since the text information area 30 is imaged only for a sample slide provided with this provisional ID number (that is, only for a sample plate 25 that has been misread by the first reading means 42), and the text information area 30 is not imaged for a normal sample plate 25 that has been successfully read by the first reading means 42, the memory range required to store the image data of the text information area 30 can be kept to a minimum.

The present invention is not limited to the previously described embodiment.

For example, the imaged text information area 30 is not only output as image data, the text entered by a printer or manually in the text information area can be imaged, and the text can be identified by reference to previously stored patterns based on the image, so as to be used as text data output for optical character recognition (OCR). In this case, the text information area 30 can be output as image data and text information. Thus, the output text information is one type of image displayed in the display box 62 for the text information area 30.

Furthermore, the first reading means 42 and the second reading means 43 may be combined as a single camera. In the case of a combined camera, a two-dimensional barcode of the code display part 42 is read normally, and the text information area 30 is imaged by moving the imaging range when the reading can not be performed.

Although the present embodiment is an example of the present invention applied to an automatic analyzer 5 capable of outputting both blood sample images and analysis results, the present invention is also applicable to devices capable of outputting only one or another of such data. That is, the automatic analyzer 5 may be a sample imaging apparatus that outputs imaged blood sample images to the display device 54, printer, or other computer or the like for visual analysis by the user of the apparatus, or may be a sample analyzing apparatus that analyzes blood based on the imaged image without displaying the imaged blood sample image on the display device 54, then subsequently outputs analysis results of blood sample images to the display device 54 and the like.

Furthermore, the present invention may be applied to devices that use biological fluids other than blood, such as bone marrow fluid and urine, as objects of analysis or imaging.

In the automatic analyzer 5 of the embodiment described above, a provisional ID number (ERR00) is provided that can be distinguished from normal ID information, the text information area 30 is imaged only for a sample plate 25 that has been provided with a provision ID number, and imaging of the text information area 30 is not performed for normal sample slides 25 that have been successfully read by the first reading means 42; however, the text information area 30 of a sample plate 25 may be imaged regardless of the normal ID information.

In the automatic analyzer 5 of the embodiment described above, a blood image taken by the automatic imaging device 10, the ID number or provisional ID number of the sample plate 25, the text information area 30 of the sample plate 25 imaged by the second reading means 43, and the WBC (white blood cell) classification results of the classification by the blood image analyzer 11 are displayed on the display screen for displaying the blood cell image data, blood identification number and blood classification results; however, it is also possible that any one among (1) the ID number or provisional ID number, (2) text information area 30 (displayed when the ID number can not be read), and (3) the blood image and classification results may be displayed.

Furthermore, although the blood image and analysis results as well as the identification information are displayed on the display device (output means) 54 provided in the blood image analyzer 11 in the automatic analyzer 5 of the above embodiment, the image data and analysis results may be displayed on a display device (output means) attached to the host computer 7 or a client PC.

What is claimed is:

1. A sample imaging apparatus comprising:
a sample image obtainer for obtaining an image of a sample smeared on a sample holder, the sample holder comprising an identification part which comprises identification information of the sample;
an identification detector for detecting the identification information;
an identification part image obtainer for obtaining, only when the identification detector can not detect the identification information, an identification part image comprising an image of at least a portion of the identification part;
an output device; and
a controller for controlling the output device, such that the image of the sample and the identification part image are output when the identification detector can not detect the identification information, and the image of the sample and the identification information are output when the identification information is detected by the information detector.

2. A sample imaging apparatus comprising:
a sample image obtainer for obtaining an image of a sample smeared on a sample holder, the sample holder comprising an identification part which comprises identification information of the sample;
an identification detector for detecting the identification information;
an identification part image obtainer for obtaining an identification part image comprising an image of at least a portion of the identification part;
an output device; and
a controller for controlling the output device, such that the image of the sample and the identification part image are output when the identification detector can not detect the identification information, wherein the controller controls the identification part image obtainer so as to obtain the identification part image only when the identification detector can not detect the identification information.

3. The sample imaging apparatus of claim 2, wherein the identification part comprises a text information area comprising text information for identifying the sample, and wherein the identification part image obtainer obtains an image of the text information area.

4. The sample imaging apparatus of claim 3, wherein the text information represents the identification information.

5. The sample imaging apparatus of claim 3, wherein the identification part further comprises a barcode which comprises the identification information.

6. The sample imaging apparatus of claim 5, wherein the identification detector comprises a barcode reader for reading the barcode, and wherein the identification part image obtainer comprises an imaging device for obtaining the image of the text information area.

7. The sample imaging apparatus of claim 2, wherein the identification detector and the identification part image obtainer are configured from a common imaging device.

8. A sample imaging apparatus comprising:
a sample image obtainer for obtaining an image of a sample smeared on a sample holder, the sample holder comprising an identification part which comprises identification information of the sample;
an identification detector for detecting the identification information;
an identification part image obtainer for obtaining an identification part image comprising an image of at least a portion of the identification part;
a first controller configured to assign provisional identification information that is different from the identification information to the sample when the identification detector can not detect the identification information;
an output device; and
a second controller for controlling the output device, such that the image of the sample and the identification part image are output when the identification detector can not detect the identification information, wherein the second controller further controls the output device so as to output the provisional identification information when the identification detector can not detect the identification information.

9. The sample imaging apparatus of claim 2, wherein the sample holder further comprises:
a printing section on which the identification information is printed; and
a sample smearing section on which the sample is smeared.

10. The sample imaging apparatus of claim 2, further comprising:
a sample analyzing section for analyzing the sample based on the image of the sample obtained by the sample image obtainer.

11. A sample analyzing system comprising:
the sample imaging apparatus of claim 10;
a smeared sample preparing apparatus for smearing the sample on the sample holder; and
a sample transfer apparatus for transferring the sample holder on which the sample is smeared from the smeared sample preparing apparatus to the sample imaging apparatus.

12. A sample analyzing apparatus comprising:
the sample imaging apparatus of claim 10; wherein
the controller controls the output device, such that an analysis result obtained by the sample analyzing section and the identification part image obtained by the identification part image obtainer are output when the identification detector can not detect the identification information.

13. The sample analyzing apparatus of claim 12, wherein when the identification information is detected by the identification detector, the analysis result and the identification information are output, and wherein when the identification detector can not detect the identification information, the analysis result and the identification part image are output.

14. The sample analyzing apparatus of claim 12, wherein when the identification information is detected by the identification detector, the analysis result, the identification information, and the identification part image are output, and wherein when the identification detector can not detect the identification information, the analysis result and the identification part image are output.

15. A sample imaging apparatus comprising:
a sample image obtainer for obtaining an image of a sample smeared on a sample holder, the sample holder comprising an identification part which comprises identification information of the sample;
an identification detector for detecting the identification information;
an identification part image obtainer for obtaining an identification part image comprising an image of at least a portion of the identification part;
an output device; and
a controller for controlling the output device, such that the image of the sample and the identification part image are output only when the identification detector can not detect the identification information, wherein
when the identification information is detected by the identification detector, the image of the sample and the identification information are output while the identification part image is not output.

16. A sample imaging method for obtaining an image of a sample smeared on a sample holder, comprising:
determining whether identification information of the sample can be detected from an identification part of the sample holder;
obtaining an identification part image comprising an image of at least a portion of the identification part at least when the identification information can not be detected;
obtaining an image of the sample; and
outputting the image of the sample and the identification part image when the identification information can not be detected, wherein
the obtaining of an identification part image is executed only when the identification information can not be detected by the attempting.

17. The sample imaging method of claim 16, further comprising:
outputting the image of the sample and the identification information when the identification information can be detected.

18. The sample imaging method of claim 16, further comprising:
outputting the image of the sample, the identification information, and the identification part image when the identification information can be detected.

19. The sample imaging method of claim 16, further comprising:
receiving an input of the identification information from an observer of the sample,
wherein the identification information is recognized based on the identification part image.

20. A sample imaging method for obtaining an image of a sample smeared on a sample holder, comprising:
determining whether identification information of the sample can be detected from an identification part of the sample holder;
obtaining an image of the sample; and
responsive to a determination that the identification information of the sample can not be detected:
assigning provisional identification information that is different from the identification information to the sample; and
outputting the provisional identification information and the obtained image of the sample.

* * * * *